(12) United States Patent
Gadelle et al.

(10) Patent No.: US 9,719,994 B2
(45) Date of Patent: Aug. 1, 2017

(54) METHOD FOR DETECTING AN INFECTION BY THE HEPATITIS C VIRUS

(71) Applicant: BIO-RAD INNOVATIONS, Marnes la Coquette (FR)

(72) Inventors: Stephane Gadelle, Vauhallan (FR); Francois Rieunier, Bois d'Arcy (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 78 days.

(21) Appl. No.: 14/366,368

(22) PCT Filed: Dec. 19, 2012

(86) PCT No.: PCT/FR2012/053001
§ 371 (c)(1),
(2) Date: Jun. 18, 2014

(87) PCT Pub. No.: WO2013/093345
PCT Pub. Date: Jun. 27, 2013

(65) Prior Publication Data
US 2014/0335508 A1   Nov. 13, 2014

(30) Foreign Application Priority Data
Dec. 20, 2011   (FR) .................. 11 61981

(51) Int. Cl.
G01N 33/53      (2006.01)
G01N 33/569     (2006.01)
C07K 14/005     (2006.01)

(52) U.S. Cl.
CPC ..... G01N 33/56983 (2013.01); C07K 14/005 (2013.01); C12N 2770/24222 (2013.01); G01N 2333/186 (2013.01); G01N 2469/10 (2013.01); G01N 2469/20 (2013.01)

(58) Field of Classification Search
None
See application file for complete search history.

(56) References Cited

U.S. PATENT DOCUMENTS 7,364,860 B2 * 4/2008 Rieunier .......... C07K 14/005
                                                    424/218.1
8,865,398 B2   10/2014 Rodgers et al.
2004/0072267 A1  4/2004 Rieunier et al.

FOREIGN PATENT DOCUMENTS

WO   WO 03/095968    11/2003
WO   WO 2008/027942   3/2008
WO   WO 2008/070727   6/2008

OTHER PUBLICATIONS

Ansaldi, F. et al. "Combination hepatitis C virus antigen and antibody immunoassay as a new tool for early diagnosis of infection" *Journal of Viral Hepatitis*, Jan. 1, 2006, pp. 5-10, vol. 13, No. 1.

Alzahrani, A. "Simultaneous Detection of Hepatitis C Virus Core Antigen and Antibodies in Saudi Drug Users Using a Novel Assay" *Journal of Medical Virology*, Apr. 1, 2008, pp. 603-606, vol. 80, No. 4.

Dean, L. et al. "Evaluation of Murex HCV Ag/Ab Combination" *Health Protection Agency*, Feb. 2007, pp. 1-18, XP-002678171.

Tu, B. et al. "Generation and Characterization of Chimeric Antibodies against NS3, NS4, NS5, and Core Antigens of Hepatitis C Virus" Clinical and Vaccine Immunology, Jun. 1, 2010, pp. 1040-1047, vol. 17, No. 6.

* cited by examiner

*Primary Examiner* — Stacy B Chen
(74) *Attorney, Agent, or Firm* — Saliwanchik, Lloyd & Eisenschenk

(57) ABSTRACT

The invention relates to a method of in-vitro detection of an infection with a hepatitis C virus (HCV) in a biological sample, comprising the simultaneous detection of the HCV capsid protein and of an antibody directed against said capsid protein, said method using, for capturing the anti-capsid antibodies, a peptide comprising an antigenic fragment derived from the truncated HCV capsid. The invention also relates to the peptide for capturing the anti-capsid antibodies and the kits comprising it.

13 Claims, No Drawings

METHOD FOR DETECTING AN INFECTION BY THE HEPATITIS C VIRUS

CROSS-REFERENCE TO RELATED APPLICATION

This application is the U.S. national stage application of International Patent Application No. PCT/FR2012/053001, filed Dec. 19, 2012.

The invention relates to the in-vitro detection of infection with a hepatitis C virus (HCV), and to the use, for this purpose, of an antigenic peptide derived from the capsid protein of the virus.

TECHNOLOGICAL BACKGROUND OF THE INVENTION

Infection with the hepatitis C virus is a worrying health problem that has long been recognized, in particular in blood transfusion.

To reduce post-transfusion risks, it is necessary to detect the presence of the virus itself, before antibodies appear, and as soon as possible after contamination. This period between contamination and seroconversion (i.e., the appearance of antibodies) is called the "serological window".

With a view to having a method that is simple, sensitive, specific, reproducible, inexpensive and easy to use, and can be automated for mass screening for detecting, firstly, the HCV antigen during the serological window period, and then for monitoring the serological evolution of the patient after seroconversion, detection of the anti-HCV antibodies, combined with detection of an HCV antigen, has been proposed.

However, this poses a major problem, that of interference between the anti-HCV antibodies present in the serum and labelled anti-HCV antibodies. Thus, the introduction on a solid phase, for the purpose of detecting a given antibody, of a target antigen having the same epitopes as those recognized by the labelled antibody or antibodies used for simultaneous, sandwich detection of an antigen would lead irreversibly to fixation of labelled antibody/antibodies on the solid phase and therefore a false positive response of the test.

This is particularly true in a system for simultaneous detection, on the same solid phase, of anti-HCV capsid antibodies and of HCV capsid antigen. Thus, deposition on the solid phase, for the purpose of detecting anti-HCV capsid antibodies, of a capsid antigen that has the same epitopes as those recognized by the labelled anti-HCV capsid antibody or antibodies used for detecting the capsid antigen leads to fixation of labelled antibody/antibodies on the solid phase and results in a false positive response of the test.

To tackle the problem of interference, application EP 1 020 727 (Advanced Life Science Institute) proposes a method for simultaneous measurement of the HCV capsid antigen and of anti-HCV capsid antibodies (a test of the "Combo" type), in which the antigen is captured and labelled by antibodies directed against capsid epitopes different from the capsid epitopes serving simultaneously for capture and detection of anti-capsid antibodies. A representative example is given where, in the simultaneous assay for sandwich detection of the antigen and of the antibodies in indirect assay, for detecting the antigen, a first (capture) antibody is used, directed against the epitopes of the sequence from amino acid (AA) 100 to amino acid 130 of the HCV capsid, and a second (detection) antibody, directed against the epitopes of the sequence AA40-50, and, for detecting the antibodies, the capture antigen used contains, for its part, the sequences AA1-42 and AA66-80.

Patent application WO 01/96875 (CHIRON) describes, among others, an assay for simultaneous detection of the capsid and of the anti-NS3 and NS4 antibodies, employing N-laurylsarcosine as detergent. It mentions an assay for simultaneous detection of the capsid antigen (in sandwich) and of anti-capsid and anti-non-structural HCV protein antibodies (in sandwich, double-antigen). For capturing the antigen, two antibodies are used, c11-3 and c11-7, which are reputed to recognize an extensive N-terminal portion (AA 10-53) of the HCV capsid, and for detection, a third antibody, c11-14, which is reputed to recognize a C-terminal portion (AA 120-130) of the HCV capsid. For detecting the antibodies, the capture antigen used is a fusion antigen with multiple epitopes which contains, fused with a fragment of superoxide dismutase ("SOD"), antigens NS3, NS4, NS5 and series of the capsid sequences from several strains of HCV: AA 9-53, bearing the R47L mutation, AA 64-88 and AA 67-84.

Patent application EP 1 251 353 (Ortho-Clinical Diagnostics) describes a "Combo complete" assay using the same antibodies for detecting the capsid, but without stating their origin or their epitope specificity. The anti-capsid antibodies are detected by means of a capsid antigen that has been modified (by mutagenesis): C22KSNV47, 48 (fusion protein with SOD comprising the deleted capsid sequence AA 10-99 of amino acids 47 and 48) or C22KSR47L (fusion protein with SOD comprising the capsid sequence AA 10-99, with a leucine replacing an arginine in position 47). Patent application WO2003/002749 (Abbott) describes many antigens and assays for detecting the HCV capsid antigen. The only "Combo complete" assay that it describes, under the name of "Real Combo", employs a biotinylated peptide corresponding to amino acids 11-28 of the capsid, immobilized in the solid phase, for detecting anti-capsid antibodies. For detecting the capsid, it employs the combination of Advanced Life Science Institute antibody C11-14 (recognizing the capsid sequence AA 45-50) in the solid phase and C11-10 (recognizing the capsid sequence AA 32-36) labelled with acridine. Application WO 03/002749 therefore performs capture of the capsid antigen and capture of the anti-capsid antibodies via two capsid sites that are clearly separate, i.e., not superposed (AA 11-28 for detecting the antibodies and anti-AA 32-36 antibodies and AA 45-50 for detecting the antigen).

Patent application EP 1 310 512 (Ortho-Clinical Diagnostics) describes the use of peptides containing a mutated capsid sequence, eliminating the possibility of binding to HCV-specific mouse monoclonal antibodies, used in a test for detecting HCV infection.

The authors of the invention described in patent application WO2003/095968 made certain epitopes of the target antigens used for capturing the antibodies artificially different, by structural modification. The epitopes thus modified are then destroyed. Simultaneously, the antibodies used for capturing and/or detecting the antigens are for their part selected so that they recognize precisely unmodified epitopes present on the patient's antigens, and so that they therefore cannot bind to the modified antigens, which no longer have these same epitopes. Since the epitopes are no longer identical, there is no longer competition between the antibodies used for capturing and/or detecting the HCV antigen and the patient's antibodies. Patent application WO2003/095968 more precisely describes an HCV capsid peptide mutated in at least two separate epitope sites, and notably the peptide 1-75 (G34-G44-G47).

SUMMARY OF THE INVENTION

The inventors now propose an even more advantageous method of detecting an HCV infection.

While avoiding the problem of interference, the method has excellent sensitivity, and permits early detection, while allowing the patient's serological evolution after seroconversion to be monitored.

More precisely, the invention provides a method of in-vitro detection of infection with a hepatitis C virus (HCV) in a biological sample, comprising the simultaneous detection of the HCV capsid protein, and of an antibody directed against said capsid protein, said method employing, for capturing the anti-capsid antibodies, a peptide comprising an antigenic fragment derived from the truncated HCV capsid.

Thus, one object of the invention is a method of in-vitro detection of an infection with a hepatitis C virus (HCV) in a biological sample, comprising the simultaneous detection of the HCV capsid protein and of an antibody directed against said capsid protein present in the biological sample, said method comprising a) bringing the biological sample into contact with a capture antibody directed against said capsid protein, and a capture antigen capable of capturing the anti-capsid protein antibodies present in the sample; b) incubating the mixture in conditions permitting the formation of antigen-antibody complexes; and c) detecting the antigen-antibody complexes formed, which optionally employs a labelled detection antibody capable of binding to the captured capsid protein and/or optionally also a labelled detection antigen capable of binding to the antibody directed against the captured capsid, characterized in that said capture antigen is a peptide comprising, or consisting of, an antigenic fragment derived from the HCV capsid from, at most, amino acid 1 to amino acid 44, said antigenic fragment comprising, or consisting of, i) a sequence from amino acids 6 to 37 of the HCV capsid protein, and having at least one point mutation of at least one amino acid at positions 33 to 36, and preferably of the amino acid in position 34, or ii) a homologous sequence of the latter.

Another object of the invention is a peptide comprising said antigenic fragment.

Another object of the invention is a kit to be used for detecting an infection with an HCV virus in a biological sample, comprising said peptide as a capture antigen of the anti-HCV capsid antibodies.

DETAILED DESCRIPTION OF THE INVENTION

Definitions

Here, the term "hepatitis C virus" or "HCV" covers all the strains and all the types, subtypes and genotypes of the virus responsible for hepatitis C. The method of the invention aims in fact to detect any HCV infection, whatever its origin and its genotype. This comprises in particular the well-known types and subtypes of the virus circulating in Europe, the United States, Japan, etc. (i.e., the 6 major genotypes: 1, 2, 3, 4, 5, 6 and their subtypes 1a, 1b, 3a, etc.). See Stuyver et al. (1994); Bukh (1995).

The HCV capsid protein is a protein of 191 amino acids, of sequence SEQ ID NO:1:

```
  1  mstnpkpqrk tkrntnrrpq dvkfpgggqi vggvyllprr
     gprlgvratr ktsersqprg
 61  rrqpipkarq pegrawaqpg ypwplygneg mgwagwllsp
     rgsrpswgps dprrrernlg
121  kvidtltcgf adlmgyiplv gaplggaara lahgvrvled
     gvnyatgnlp gcsfsiflla
181  llscltipas a
```

Unless stated otherwise, the amino acids are localized in the capsid protein with reference to sequence SEQ ID NO:1, which is a consensus sequence of genotype 1 (subtypes 1a, 1b, 1c).

Several epitopes of the capsid protein have been identified. Notably the epitopes localized between amino acid 16 and amino acid 40 are known.

The expression "from, at most, amino acid 1 to amino acid 44" means that the peptide with at most 44 amino acids does not extend beyond amino acid 44 of sequence SEQ ID NO:1, but can optionally be shorter, provided it contains the sequence 6-37 (still referring to SEQ ID NO:1).

In the context of the invention, a "biological sample" preferably consists of a biological fluid, such as blood, plasma, serum, urine, cerebrospinal fluid, saliva, etc.

The term "antibody" refers to any whole antibody or functional fragment of an antibody comprising or consisting of at least one antigen recognition site, allowing said antibody to bind to at least one antigenic determinant of an antigenic compound. As examples of antibody fragments, we may mention the fragments Fab, Fab', and F(ab')2 as well as the chains scFv (single chain variable fragment), dsFv (double-stranded variable fragment), etc. These functional fragments can notably be obtained by genetic engineering.

The production of monoclonal antibodies or of monospecific polyclonal sera useful in the context of the invention is based on conventional techniques, the details of which are given later.

"Capture antibody" means an antibody or a part of an antibody, preferably fixed on a solid phase, which is capable of retaining an HCV antigen present in a biological sample by affine binding.

The presence of antibodies and antigens in the biological sample is revealed by specific markers. Regarding detection of the antigen, the invention notably envisages detection by means of at least one "detection antibody". Said labelled "detection antibody" is capable of binding to the captured antigen by affine binding, recognizing an epitope site different from that recognized by the capture antibody. Regarding detection of the antibodies, labelled anti-immunoglobulin, or anti-isotype, antibodies can notably be used, for example anti-immunoglobulin G in an indirect ELISA format or labelled antigens in a sandwich format.

The capture antibody and/or detection antibody recognizes the natural epitope of portion 33-36 of the HCV capsid protein.

The term "labelled" refers both to direct labelling (via enzymes, radioisotopes, fluorochromes, luminescent compounds, etc.) and to indirect labelling (for example, via antibodies themselves labelled directly or by means of reagents of a labelled "affinity pair", such as, but not exclusively, the labelled avidin-biotin pair, etc.).

"Capture antigen" means an isolated antigenic fragment, preferably fixed on a solid phase, which is capable of being recognized by anti-HCV antibodies and of permitting affine binding with the latter.

"Detection antigen" means a labelled antigen. It makes it possible either to detect the captured antigen by competition, or to detect antibodies by a conventional antigen-antibody-antigen sandwich technique, also called the "double antigen sandwich" method (Maiolini et al. (1978)).

The term "specific" or "specifically", when it refers to a recognition or a specific binding of an antibody for an antigen, signifies that the antibody interacts with the antigen without substantial interaction with other antigens, or if we are talking of "specific" recognition with an epitope, by quasi-exclusive recognition of this epitope. Association constants above $10^8$ L. $mol^{-1}$ are preferable.

The term "homologue" refers to a peptide comprising an antigenic fragment derived from the HCV capsid of at most 44 amino acids. This antigenic fragment comprises a sequence differing from the sequence ranging at most from amino acids 1 to 44 of the HCV capsid protein, by a conservative substitution of one or more amino acids, or a deletion of one or more amino acids at the N-terminal end (amino acids 1 to 5) and/or C-terminal end (amino acids 38 to 44).

Capture and Detection Antibodies and Antigens

The antibodies used in the present invention are specific antibodies of the antigen, and, for this reason, are monoclonal antibodies or monospecific polyclonal antibodies, i.e., they only recognize one epitope specifically.

The method of the invention relates more particularly to the detection of anti-capsid antibodies, and employs capture antigens that fix the anti-capsid antibodies present in the biological sample.

The peptide intended for capturing the anti-capsid antibodies comprises an antigenic fragment derived from the HCV capsid ranging at most from amino acids 1 to 44, said antigenic fragment comprising a sequence from amino acids 6 to 37 of the HCV capsid protein, or a homologous sequence of the latter. It is therefore understood that the capture antigen according to the invention lacks amino acids 45 to 191 (which are normally present in the HCV capsid protein). According to a particular embodiment, the amino acid sequence of the peptide useful as a capture antigen according to the invention comprises or consists of 32 to 44 amino acids, for example consists of a sequence of 44 amino acids.

The peptide has at least one point mutation of at least one amino acid in the sequence 33-36, and preferably of the amino acid in position 34. It can be a substitution with any non-conservative amino acid. For amino acid 34, an amino acid preferably different from an isoleucine, leucine, methionine, phenylalanine or alanine residue is used. Preferably, an uncharged amino acid is selected. Preferably, the amino acid valine in position 34 is substituted with a glycine.

Owing to the mutation of the capture antigenic peptide, there is no interference between the immobilized antigen-anti-capsid antibody reaction of the sample and the immobilized antibody-capsid antigen reaction of the sample.

According to a preferred embodiment, the capture antibody immobilized on the solid phase is an antibody directed against the natural epitopes 33-36 of the capsid protein, whereas the detection antibody at c1), labelled directly or indirectly, is directed against an epitope different from the natural epitopes present in portions 33 to 36, more generally 6 to 37, of said HCV capsid protein. For example it can be an antibody directed against epitopes 44-47 of the capsid.

According to another preferred embodiment, the capture antibody immobilized on the solid phase is an antibody directed against an epitope different from the natural epitopes present in portions 33 to 36, more generally 6 to 37, of said HCV capsid protein—for example it can be an antibody directed against epitopes 44-47 of the capsid, whereas the detection antibody at c1), labelled directly or indirectly, is an antibody directed against the natural epitopes 33-36 of the capsid protein.

According to a particular embodiment, the capture antigen is a peptide consisting of sequences 1 to 44 of the HCV capsid protein, and having a point mutation of the amino acid in position 34, preferably a substitution to glycine.

A preferred example is therefore the peptide of sequence SEQ ID NO:2.

$_1$MSTNPKPQRKTKRNTNRRPQDVKFPGGGQIVGG$_{34}$YLLPRRGPRL

A homologous peptide, consisting of a sequence as defined above, but additionally truncated from 1 to 5 amino acids on the N-terminal or C-terminal side, can also be used. Thus, the peptides 6-37 can be used, having a point mutation of at least one amino acid in sequences 33-36, and preferably of the amino acid in position 34. Preferably it is the peptide of sequence SEQ ID NO:3.

$_6$KPQRKTKRNTNRRPQDVKFPGGGQIVGG$_{34}$YLL$_{37}$

Peptides only differing from the above peptides by conservative substitution are also comprised in the invention.

The expression "conservative substitution" expresses any replacement of one amino acid residue with another, without altering the general conformation or the antigenicity of the peptide. Conservative substitution includes, but is not limited to, replacement with an amino acid having similar properties (for example shape, polarity, hydrogen bonding potential, acidity, basicity, hydrophobicity etc.). Amino acids having similar properties are well-known by a person skilled in the art. For example, arginine, histidine and lysine are basic hydrophilic amino acids and can be interchangeable. In the same way, isoleucine, a hydrophobic amino acid, can be replaced with a leucine, a methionine or a valine. The neutral hydrophilic amino acids that can replace one another include asparagine, glutamine, serine and threonine. "Substituted" and "modified" mean, according to the invention, amino acids that have been altered or modified relative to an amino acid found in nature.

Thus, in the context of the present invention, a conservative substitution is a substitution of one amino acid with another having similar properties. Examples of conservative substitutions are given in Table 1 below:

TABLE 1

Conservative substitutions I

| Characteristics of the side chain | Amino acid |
|---|---|
| Non-polar | G A P I L V |
| Polar, uncharged | C S T M N Q |
| Polar, charged | D E K R |
| Aromatic | H F W Y |
| Other | N Q D E |

According to Lehninger, 1975, the conservative amino acids can also be grouped as shown in Table 2 below:

TABLE 2

Conservative substitutions II

| Characteristics of the side chain | Amino acid |
|---|---|
| Non-polar (hydrophobic) | |
| A. Aliphatic: | A L I V P |
| B. Aromatic: | F W |
| C. Containing a sulphuryl: | M |
| D. Other | G |
| Polar, uncharged | |
| A. Hydroxyl: | S T Y |
| B. Amides: | N Q |
| C. Sulphydryl: | C |
| D. Other | G |
| Positively charged (basic) | K R H |
| Negatively charged (acidic) | D E |

Yet another alternative conservative substitution is presented in Table 3 below:

TABLE 3

Conservative substitutions III

| Original residue | Example of substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (Y) |
| Tyr (Y) | Trp (W), Phe (F), Thr (T), Ser (S) |
| Val (V) | Ile (I), Leu (L), Met (M), Phe (F), Ala (A) |

The peptides according to the invention can be prepared by all the classical techniques of peptide synthesis, namely by chemical synthesis or genetic recombination. In a preferred embodiment, the peptides are obtained by chemical synthesis. More preferably, the peptides are obtained either by successive condensation of the amino acid residues in the required order, or by condensation of the residues on a fragment previously formed and already containing several amino acids in the appropriate order, or by condensation of several fragments previously prepared, taking care to protect, beforehand, all the reactive functions carried by the amino acid residues, except the amine and carboxyl functions inserted in the peptide bond during condensation, and notably by Merrifield's technique of solid phase synthesis, which is advantageous for reasons of purity, antigenic specificity, absence of unwanted by-products and for its ease of implementation (Merrifield, (1963); R. C. Sheppard (1971); Atherton et al. (1989)). As an automatic synthesizer, it is possible to use the "9050 Plus Pep Synthesizer" from Millipore, the "Pioneer" synthesizer from PerSeptive, the "433A" synthesizer from ABI (Applied Biosystems, Inc.) or the "Symphony" synthesizer from Rainin. The peptides can also be obtained by homogeneous phase synthesis.

The antigenic peptide intended for capturing the anti-capsid antibodies can be prolonged at its N-terminal end with a spacer.

The invention also relates to said conjugated peptide comprising the antigenic peptide, bound covalently, at its N-terminal end, to a spacer.

"Spacer" means a molecule which is preferably a peptide, preferably from 1 to 8 amino acids, preferably functionalized, i.e., having thiol, hydrazide, aldehyde functions, or a biotin, for example. It is generally a peptide of 1 to 8 amino acids, which can comprise non-natural amino acids, such as ω-amino acids. Preferably said spacer contains at least one cysteine residue. According to a preferred embodiment, the spacer is C-Hx, where C is a cysteine and Hx is 6-amino-hexanoic acid. According to another embodiment, the spacer is the peptide of sequence CGG.

The capture peptide can be coupled covalently to itself or it can be coupled to a carrying molecule via the spacer. The spacer thus makes it possible to optimize the attachment of the antigenic peptide on a solid surface, a protein or a soluble functionalized polymer and/or makes it possible to conjugate several antigenic molecules. Preferably, the carrying molecule is a protein such as bovine serum albumin (BSA) or ovalbumin. According to another embodiment, the peptide is bound, via the spacer, to an amino-dextran.

Thus, according to a particular embodiment, the peptide conjugate comprises a spacer bound covalently to several antigenic peptides, which may be identical or different. Preferably a homodimer is thus formed.

Especially preferably, the capture antigen of the anti-capsid antibodies is only one antigenic peptide as defined above (for example the peptide of sequence SEQ ID NO:2).

However, in a particular embodiment, the capture antigen according to the invention, as defined above (for example the peptide of sequence SEQ ID NO:2), can be used in combination with another capture antigen (preferably present on the same solid phase as the capture antigen according to the invention) whose amino acid sequence comprises or consists of a fragment of the HCV capsid protein ranging from amino acids 45 or 46 to one of the amino acids between 60 and 80, preferably between 65 and 75 or between 68 and 75 (still referring to SEQ ID NO:1). In a more particular embodiment, the additional capture antigen consists of the sequence 45-65, 45-66, 45-67, 45-68, 45-69, 45-70, 45-71, 45-72, 45-73, 45-74, or 45-75, or the sequence 46-65, 46-66, 46-67, 46-68, 46-69, 46-70, 46-71, 46-72, 46-73, 46-74, or 46-75. As examples, we may mention the peptide 45-65, the peptide 45-68 or, more preferably, the peptide 45-75.

Moreover, detection of the anti-capsid antibodies can be combined with the detection of antibodies to another HCV protein. Various capture, or detection, antigens can be combined together. This embodiment, which employs several different capture, and/or detection, antigens, allows for example the simultaneous detection of anti-capsid antibodies and of anti-non-structural protein antibodies, for example NS3 and/or NS4 or NS5 of HCV. Simultaneous detection of anti-capsid antibodies and of anti-NS3 antibodies is particularly preferred. The invention also comprises simultaneous detection of capsid antigens, of anti-capsid antibodies, of anti-envelope structural protein E1 and/or E2 antibodies, of envelope E1 and/or E2 antigens, and/or of anti-non-structural proteins NS3 and/or NS4 or NS5 of HCV antibodies. Other conceivable combinations also form part of the invention.

Methods of Detection

The method of the invention comprises simultaneous detection of the HCV capsid protein, and of an antibody directed against said capsid protein, present in the biological sample, said method comprising a) bringing the biological sample into contact with a capture antibody directed against said capsid protein and a capture antigen capable of capturing anti-capsid protein antibodies present in the sample; b) incubating the mixture in conditions permitting formation of antigen-antibody complexes; and c) detecting the antigen-antibody complexes formed, which optionally employs a labelled detection antibody capable of binding to the captured capsid protein and/or optionally also a labelled detection antigen capable of binding to the antibody directed against the captured capsid.

In general, and unless stated otherwise, the capture antigen refers here both to the antigenic fragment derived from the HCV capsid from, at most, amino acid 1 to amino acid 44, and to a conjugated peptide comprising said fragment, as described above.

The biological sample can optionally be treated in a preliminary step, or can be brought into contact with the capture antigen and the capture antibody in conditions promoting exposure of the antigens to be detected.

Advantageously, the sample is treated with a denaturing agent before detection, and preferably before it is brought into contact with the antibodies used. This denaturing agent can notably consist of one or more detergents of the non-ionic type, such as Tween 20, Triton X-100, Nonidet P-40 (NP40) (tert-octylphenoxy poly(oxyethylene) ethanol, also called IGEPAL CA630), n-octyl beta-D-glucopyranoside, or an acidic solution.

This combined immunoassay can be performed according to various formats that are well-known by a person skilled in the art: in solid phase or in homogeneous phase; once or twice; in a double sandwich method (sandwich for both detections of antigens and of antibodies); or in an indirect method (for detecting antibodies) combined with a sandwich method (for detecting antigen), as non-limiting examples.

According to a preferred embodiment, the capture antibody and the capture antigen are immobilized on a solid phase. As non-limiting examples of a solid phase, it is possible to use microplates, in particular polystyrene microplates, such as those marketed by Nunc (Denmark). It is also possible to use solid particles or beads, paramagnetic beads, such as those supplied by Dynal or Merck-Eurolab (France) (under the brand name Estapor), test tubes of polystyrene or polypropylene, or a nitrocellulose membrane, etc.

An immunoassay format of the sandwich type between two antibodies (for capture and for detection) is particularly advantageous for detecting the antigens present in the biological sample, whereas the antibodies can be detected by employing a capture antigen and a labelled conjugate which is fixed on the antibody (according to a format commonly called "indirect format"), for example the labelled protein A or a labelled anti-immunoglobulin, or anti-isotype, antibody. It is also possible to detect the antibodies advantageously by employing a capture antigen and a labelled antigen which are fixed on the antibody (according to a format designated as "antigen-antibody-antigen sandwich" or "double antigen sandwich").

An immunoassay format for detecting the antigens by competition is also possible. Other types of immunoassay can also be envisaged and are well-known by a person skilled in the art.

The simultaneous detection of the HCV antigen and of the anti-HCV antibodies according to the invention can be performed once, namely by simultaneously bringing into contact the biological sample and the detecting means, such as the detection antibody or antibodies, at the same time as the capture antibody or antibodies and the capture antigen or antigens. In this case, the immunoassay for detecting the antigen and the immunoassay for detecting the antibodies are both preferably performed in a sandwich. Alternatively, the detecting means, such as the detection antibody or antibodies, can be added to the mixture secondly, i.e., after the first antigen-antibody complexes have formed. This is then called a two-step assay.

According to a preferred embodiment of the invention, the method of detecting infection with the hepatitis C virus (HCV) in a biological sample comprises: a) bringing the sample into contact with a capture antibody of the HCV capsid protein and a capture antigen of the anti-HCV capsid antibodies fixed on a solid phase; b) incubating the mixture in conditions permitting formation of antigen-antibody complexes; c) separating the solid phase and the liquid phase; and d) bringing the solid phase into contact with a labelled detection antibody capable of binding the captured HCV antigen and one or more labelled anti-immunoglobulin, or anti-isotype, antibodies capable of binding the captured anti-HCV antibody.

ELISA assays, radioimmunoassays, or any other detection technique can be employed for revealing the presence of the antigen-antibody complexes formed.

Detection of the presence of antigens or of antibodies in the biological sample can be supplemented with quantification, for example by measurement of the signals emitted by the markers (colour, luminescence, radioactivity, etc.), according to the standard techniques familiar to a person skilled in the art.

Kits

Kits and reagents useful for detecting an HCV infection in a biological sample, according to the method of the invention, can be supplied for simple practical application of the invention that is applicable to numerous biological samples.

The invention therefore provides a kit that can be used for detecting an infection by an HCV virus in a biological sample, comprising an antigenic peptide capable of capturing the anti-HCV capsid antibodies. The kit can further comprise means for detecting said anti-HCV antibodies present in the biological sample and complexed to said capture antigen, said detecting means preferably being a labelled anti-immunoglobulin or anti-isotype antibody.

Advantageously, said kit can contain several antigens and several capture antibodies.

The kit can in addition contain antigens of other proteins of the virus, such as NS3 and/or NS4, and/or NS5, these antigens then being intended to capture anti-NS3 and/or anti-NS4, and/or NS5 antibodies. Preferably these antigens are mixed with the capture antigen derived from the capsid.

As described above, the capture antibody and the capture antigen can be presented advantageously in immobilized form on a solid phase, such as a microplate.

A preferred kit comprises:
a1) a capture antigen, which is a peptide comprising, or consisting of, an antigenic fragment derived from the HCV capsid from, at most, amino acid 1 to amino acid 44, said antigenic fragment comprising, or consisting of, i) a sequence from amino acids 6 to 37 of the HCV capsid protein, and having at least one point mutation of the amino acid in position 34, or ii) a homologous sequence of the latter;
a2) preferably also capture antigens of the anti-non-structural protein antibodies comprising some or all of the non-structural proteins NS3, NS4, and/or NS5;

b) a capture antibody directed against the HCV capsid protein;

said capture antigen and said capture antibody being immobilized on a solid phase; and:

c1) a labelled detection antibody; and c2) an anti-immunoglobulin antibody or antibodies or optionally a labelled detection antigen, which comprises, or is, an antigenic fragment that is a peptide comprising, or consisting of, an antigenic fragment derived from the HCV capsid from, at most, amino acid 1 to amino acid 44, said antigenic fragment comprising, or consisting of, i) a sequence from amino acids 6 to 37 of the HCV capsid protein, and having a point mutation of at least one amino acid at positions 33 to 36 or ii) a homologous sequence of the latter.

The capture antibody and/or detection antibody recognizes the natural epitope of portions 33-36 of the HCV capsid protein.

According to a preferred embodiment, the capture antibody immobilized on the solid phase is an antibody directed against the natural epitopes 33-36 of the capsid protein, whereas the detection antibody at c1), labelled directly or indirectly, is directed against an epitope different from the natural epitopes present in portions 33 to 36, more generally 6 to 37, of said HCV capsid protein. For example it can be an antibody directed against epitopes 44-47 of the capsid.

According to another preferred embodiment, the capture antibody immobilized on the solid phase is an antibody directed against an epitope different from the natural epitopes present in portions 33 to 36, more generally 6 to 37, of said HCV capsid protein—for example it can be an antibody directed against epitopes 44-47 of the capsid, whereas the detection antibody at c1), labelled directly or indirectly, is an antibody directed against the natural epitopes 33-36 of the capsid protein.

The kit can further comprise a detergent, more particularly a non-ionic detergent, known by a person skilled in the art.

The following examples illustrate the invention without limiting its scope.

Examples: Detection of an Infection with the Hepatitis C Virus

Materials for the Assay Protocol:
1) Solid phase selected: Maxisorp microplate, Nunc (Denmark).
2) Anti-capsid monoclonal antibody-biotin conjugate ("acm-POD"): a conjugate of the anti-capsid monoclonal antibody Acm 2 labelled with peroxidase is prepared according to the protocol described in patent application EP 0 752 102.
Another anti-capsid monoclonal antibody, Acm 1, is also used.
3) Mouse anti-IgG (Fc$_\gamma$) human polyclonal antibody-POD conjugate: this conjugate is obtained from Jackson Immunoresearch Laboratories, USA (indirect ELISA format). Biotin-labelled capsid peptide conjugate (sandwich format).
4) Diluents for the 1st and 2nd steps of the protocols according to the invention:
Diluent for the 1st step: Tris buffer, NaCl 0.05M, at pH 6.7 with addition of IGEPAL CA 630 (Sigma) at 0.25%.
Diluent for the 2nd step: citrate buffer (50 mM), at pH 6.7, solution in glycerol at 20%.

5) Development solution: the development solution was composed of:
5a) a substrate buffer: solution of citric acid (0.075M) and sodium acetate (0.1M) at pH 4.0, containing $H_2O_2$ at 0.015% and dimethylsulphoxide (DMSO) (PROLABO) at 4%, and
5b) a chromogen: solution containing tetramethylbenzidine (TMB) (8 mM), (Sigma).

Methods:

Protocol for Simultaneous Detection of the Capsid Antigen and of the Antibodies (Anti-Capsid and Anti-NS3, NS4) of the Hepatitis C Virus in a Sample (Serum or Plasma)

The principle of the assay is based on an immunoenzyme method of the sandwich type for detecting the antigen, and of the indirect type, for detecting the antibodies.

It is based on the following steps:

A sensitizing solution is first prepared:
with a mixture of HCV antigens: a mutated peptide CHx-1-44 (G34) (capsid) comprising the sequence SEQ ID NO:2 and two recombinant proteins produced by *Escherichia coli* from clones selected from the non-structural regions NS3 (AA 1192-1657) and NS4 (AA 1694-1735) and
with an anti-capsid monoclonal antibody (Acm 1) in buffer Tris 0.5M, pH 7.4. The wells of a microtitre plate (Nunc, Maxisorp) are then sensitized with the above solution at a rate of 110 µl per well.

The microtitre plates are incubated overnight at room temperature (18-24° C.).

After removing the sensitizing solution, the plates are washed with phosphate buffer (0.01M, pH 7.4) containing 0.1% of Tween 20, then saturated by adding a phosphate buffer (0.01M, pH 7) containing 5% of sucrose, 25% of skimmed milk (Candia™ France, or any other equivalent commercial skimmed milk) and 10 mM of EDTA.

100 µl of diluent for the 1st step, containing the peroxidase-labelled anti-capsid monoclonal antibody Acm 2, then 50 µl of the sample (serum or plasma), are distributed successively in each well.

The reaction mixture is incubated at 37° C. for 1.5 h. Any HCV capsid antigens that may be present become attached to the solid-phase monoclonal antibody Acm 1 and form complexes with the peroxidase-labelled anti-capsid monoclonal antibody Acm 2. Moreover, if anti-HCV antibodies are present, they bind to the antigens fixed on the solid phase.

The plates are then washed (3 times) with a washing solution (buffer Tris NaCl 0.01M, pH 7.4 with addition of Tween 20 at 0.1%). 100 µl of diluent for the 2nd step containing peroxidase-labelled anti-human IgG antibodies or the biotin-labelled capsid peptide is distributed in each well. The reaction mixture is incubated at room temperature (18-24° C.) for 30 minutes. The labelled anti-human IgG antibodies or the biotin-labelled capsid peptide in their turn become fixed to the specific antibodies retained on the solid phase.

The plates are then washed (5 times) with a washing solution (buffer Tris NaCl 0.01M, pH 7.4 with addition of Tween 20 at 0.1%). The unbound anti-human IgG conjugate is thus removed.

100 µl of a development solution (substrate buffer+chromogen) is distributed in each well. The reaction is allowed to develop in the dark for 30 minutes at room temperature (18-24° C.).

Then 100 µl of stopping solution (1N $H_2SO_4$) is distributed in each well. After stopping the reaction, the optical density is read on a spectrophotometer at 450/620 nm.

Definition of the Threshold Value:

The threshold value was determined after statistical analysis of the data for specificity and sensitivity using the ROC (Receiver Operating Characteristic) curve (Berck and Schultz, (1986)).

The specificity study was based on 5000 samples from healthy subjects and the sensitivity study was based on HCV-positive samples (notably commencement of seroconversion) from commercial panels: BBI (Boston Biomedica Company, USA), Impath (USA), Serologicals (USA), Nabi (USA), and ProMedDx (USA).

The threshold value is calculated for each plate from the signal obtained on a positive control, divided by a constant coefficient X, specific to the test. It is approx. 0.45 unit of OD (optical density) in the example presented in indirect format.

Example 1: Detection of Anti-Capsid Antibodies in Samples (Sera or Plasmas) that are Negative for HCV Antigen Three panels of seroconversion samples PHV 905, 907 and 914 (i.e., two consecutive samples of sera or plasmas, taken from two patients after HCV infection or in the course of seroconversion) that are commercially available (Serac-are Life Sciences/BBI Diagnostics, USA) were tested according to the sandwich protocol. The capsid peptide 1-44 G34 (SEQ ID NO:2) was then labelled with biotin and the complex was revealed with streptavidin-peroxidase. It is therefore a single anti-capsid detection.

These samples were found to be positive with a threshold value calculated from the mean value of three negative samples plus 6 standard deviations (OD: 0.077).

TABLE 1

| Sample | Optical density | |
|---|---|---|
| 905-08 | 0.058 | negative |
| 905-09 | 0.209 | positive |
| 907-05 | 0.480 | positive |
| 907-06 | 0.694 | positive |
| 914-08 | 0.409 | positive |
| 914-09 | 0.824 | positive |
| Neg 1 | 0.043 | negative |
| Neg 2 | 0.048 | negative |
| Neg 3 | 0.044 | negative |

The invention therefore makes it possible to detect, in subjects contaminated with HCV, samples that are positive for anti-capsid antibodies.

Example 2: Comparison of Performance and Classification of Various Techniques on Seroconversion Sera that are Positive for Antibody and/or Antigen 9 commercially-available seroconversion panels (Serac-are Life Sciences/BBI, USA; Impath, USA), having different specificities, were tested with the assay according to the invention following the protocol indicated, and the results were compared with a series of commercially-available tests. This comparison takes into account the number of days of delay in detection relative to RNA detection (PCR assay). Thus, the kit having the smallest sum gives the best performance for early detection. These panels are found to be positive for antigen and/or antibody directed against the NS3 proteins and capsid of the HCV virus (characterization carried out by the RIBA test marketed by Ortho Clinical Diagnostics).

TABLE 2

| Panel Impath/BBI | Number of days of delay of detection relative to detection by PCR | | | | Target antigen |
|---|---|---|---|---|---|
| | Invention protocol | Axsym HCV version3 (Abbott) | "Ortho HCV 3.0 short incubation" (Ortho Clinical Diagnostics) | Access HCV Ab Plus (BIO-RAD) | |
| 912 | 0 | 7 | 7 | 7 | Capsid |
| 913 | 0 | 12 | 7 | 7 | Capsid |
| 6215 | 0 | 20 | 20 | 20 | Capsid |
| Sub-total | 0 | 39 | 34 | 34 | |
| 915 | 5 | 5 | 14 | 17 | NS3 |
| 6212 | 12 | 12 | 12 | 23 | NS3 |
| 6224 | 11 | 19 | 19 | 19 | NS3 |
| 9041 | 27 | 62 | 62 | 62 | NS3 |
| 9044 | 0 | 21 | 25 | 25 | NS3 |
| 9047 | 0 | 28 | 28 | 28 | NS3 |
| Sub-total | 55 | 147 | 160 | 174 | |
| Total | 60 | 186 | 194 | 208 | |

The invention makes it possible to detect samples positive for antibody and antigen earlier than an antibody assay.

REFERENCES

Atherton et al. (1989) "Solid phase peptide synthesis, a practical approach", IRL Press, Oxford University Press, pp. 25-34

Bukh, Semin. Liver Dis. (1995) 15: 41-63

Maiolini et al., (1978) Journal of Immunological Methods, 20, pp. 25-34

Merrifield (1963) J. Amer. Chem. Soc., 85, pp. 2149-2154

Sheppard, in "Peptides 1971", Nesvadba H (ed.) North Holland, Amsterdam, p. 111

Stuyver et al. (1994), P. N. A. S. USA, 91, pp. 10134-10138

The invention claimed is:

1. A method of in-vitro detection of an infection with a hepatitis C virus (HCV) in a biological sample, comprising the simultaneous detection of the HCV capsid protein, and of an antibody directed against said capsid protein, present in the biological sample, said method comprising: a) bringing the biological sample in contact with a capture antibody directed against said capsid protein, and a capture antigen capable of capturing anti-capsid protein antibodies present in the sample; b) incubating the mixture in conditions permitting formation of antigen-antibody complexes; and c) detecting the antigen-antibody complexes formed, optionally employing a labelled detection antibody, capable of binding to the captured capsid protein and/or optionally also a labelled detection antigen, capable of binding to the captured anti-capsid antibody; wherein said capture antigen is a peptide comprising an antigenic fragment derived from the HCV capsid from, at most, amino acid 1 to amino acid 44 of SEQ ID NO: 1, said antigenic fragment comprising a sequence from amino acids 6 to 37 of the HCV capsid protein, and consisting of one or more point mutations at amino acid positions 33 to 36 of SEQ ID NO: 1 wherein said point mutation(s) results in an amino acid substitution.

2. The method according to claim 1, wherein the capture antigen is a peptide having a point of the amino acid at position 34 of SEQ ID NO: 1.

3. The method according to claim 2, wherein the capture antigen is a peptide consisting of amino acids 1 to 44 of SEQ ID NO: 1, and having a point mutation of the amino acid in position 34 of SEQ ID NO: 1.

4. The method according to claim 2, wherein valine at position 34 is substituted with a glycine residue.

5. The method according to claim 1, wherein said capture antibody and said capture antigen are immobilized on a solid phase.

6. The method according to claim 5, wherein the solid phase further comprises at least one antigen derived from an HCV protein which is not the capsid.

7. The method according to claim 1, wherein the detection antibody is added to the mixture after the antigen-antibody complexes have formed.

8. The method according to claim 1, wherein the detection antibody, and/or the detection antigen, is brought in contact with the biological sample at the same time as the capture antibody and the capture antigen.

9. The method according to claim 3, wherein the valine at position 34 is substituted with a glycine residue.

10. The method according to claim 2, wherein the valine at position 34 is substituted with an amino acid other than isoleucine, leucine, methionine, phenylalanine or alanine.

11. The method according to claim 3, wherein the valine at position 34 is substituted with an amino acid other than isoleucine, leucine, methionine, phenylalanine or alanine.

12. The method according to claim 1, wherein:
   i) glycine at position 33 of SEQ ID NO: 1 is replaced by an amino acid other than proline;
   ii) valine at position 34 of SEQ ID NO: 1 is replaced by an amino acid other than isoleucine, leucine, methionine, phenylalanine or alanine;
   iii) tyrosine at position 35 of SEQ ID NO: 1 is replaced by an amino acid other than tryptophan, phenylalanine, threonine or serine; and/or
   iv) leucine at position 36 of SEQ ID NO: 1 is replaced by an amino acid other than isoleucine, valine, methionine, alanine or phenylalanine.

13. The method according to claim 1, wherein the capture antigen consists of a single point mutation at an amino acid position selected from positions 33 to 36 of SEQ ID NO: 1 and wherein the single point mutation is selected from the following:
   i) glycine at position 33 of SEQ ID NO: 1 is replaced by an amino acid other than proline;
   ii) valine at position 34 of SEQ ID NO: 1 is replaced by an amino acid other than isoleucine, leucine, methionine, phenylalanine or alanine;
   iii) tyrosine at position 35 of SEQ ID NO: 1 is replaced by an amino acid other than tryptophan, phenylalanine, threonine or serine; or
   iv) leucine at position 36 of SEQ ID NO: 1 is replaced by an amino acid other than isoleucine, valine, methionine, alanine or phenylalanine.

*

SEQUENCE LISTING

<160> NUMBER OF SEQ ID NOS: 3

<210> SEQ ID NO 1
<211> LENGTH: 191
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Ser Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
            180                 185                 190

<210> SEQ ID NO 2
<211> LENGTH: 44
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Gly Tyr Leu Leu Pro Arg Arg Gly Pro Arg Leu
        35                  40

<210> SEQ ID NO 3
<211> LENGTH: 32
<212> TYPE: PRT
<213> ORGANISM: Hepatitis C virus

<400> SEQUENCE: 3

Lys Pro Gln Arg Lys Thr Lys Arg Asn Thr Asn Arg Arg Pro Gln Asp
1               5                   10                  15

Val Lys Phe Pro Gly Gly Gly Gln Ile Val Gly Gly Gly Tyr Leu Leu
            20                  25                  30